United States Patent [19]

Langer et al.

[11] 4,223,678
[45] Sep. 23, 1980

[54] ARRHYTHMIA RECORDER FOR USE WITH AN IMPLANTABLE DEFIBRILLATOR

[75] Inventors: Alois A. Langer, Pittsburgh, Pa.; Morton M. Mower, Lutherville, Md.

[73] Assignee: Mieczyslaw Mirowski, Owings Mills, Md.

[21] Appl. No.: 902,763

[22] Filed: May 3, 1978

[51] Int. Cl.² ............................................. A61N 1/32
[52] U.S. Cl. .................................. 128/419 D; 128/903
[58] Field of Search ......... 128/419 D, 2.06 A, 2.06 B, 128/2.06 F, 2.06 R, 2.1 A, 2.1 R

[56] References Cited

U.S. PATENT DOCUMENTS

| | | | |
|---|---|---|---|
| 3,212,496 | 10/1965 | Preston | 128/2.1 A |
| 3,547,107 | 12/1970 | Chapman et al. | 128/2.06 A |
| 3,603,881 | 9/1971 | Thornton | 128/2.1 A |
| 3,612,041 | 10/1971 | Ragsdale | 128/2.06 A |
| 3,639,907 | 2/1972 | Greatbatch | 128/2.1 A |
| 3,724,455 | 4/1973 | Unger | 128/419 D |
| 3,779,237 | 12/1973 | Goeltz | 128/2.06 A |
| 3,799,148 | 3/1974 | Rowen | 128/2.06 A |
| 3,805,795 | 4/1974 | Denniston et al. | 128/419 D |
| 3,952,750 | 4/1976 | Mirowski et al. | 128/419 D |
| 3,953,848 | 4/1976 | Dillman et al. | 128/2.1 A |
| 3,972,320 | 8/1976 | Kalman | 128/2.1 A |
| 4,005,282 | 1/1977 | Jennings | 128/2.1 R |

*Primary Examiner*—William E. Kamm
*Attorney, Agent, or Firm*—Fleit & Jacobson

[57] ABSTRACT

A device for recording and subsequently reproducing information, such as desired portions of an ECG signal produced by a heart prior to and during the occurrence of a disturbance in cardiac electrical activity. Two basic embodiments of the inventive recorder are contemplated. One embodiment is fully implantable and is encased with sensing and defibrillating electronics. With this embodiment, a low-power, low-capacity, continually updated recorder is continually operative, and a high-capacity stand-by recorder is actuated upon the sensing of fibrillation. An external device is used to retrieve by telemetry, the information stored in the implanted recorder. The second embodiment of the inventive recorder is an external device which has external electrodes for associating with the patient; ECG information is transmitted to the recorder unit by telemetry. Here, because power consumption is not so critical as with the implantable embodiment, a delay-type continually updated memory is continuously operative. Then, when any one of several types of arrhythmias is sensed, or when a defibrillating pulse is delivered, the data in the memory is "permanently" recorded on magnetic tape. Either embodiment may be used with an implantable defibrillator to record and subsequently reproduce information relating to the operation of the implantable defibrillator. The second embodiment also has an alarm capability to warn the patient should there be an interruption in telemetric transmission.

46 Claims, 5 Drawing Figures

ARRHYTHMIA RECORDER FOR USE WITH AN IMPLANTABLE DEFIBRILLATOR

BACKGROUND OF THE INVENTION

1. Field of the Invention

This invention relates to a device for recording and subsequently reproducing desired portions of an ECG signal produced by a heart prior to and during the occurrance of various disturbances in cardiac electrical activity.

2. Description of the Prior Art

During the past several decades, coronary heart disease has come to occupy the first position among the causes of death in the developed areas of the world. Although the precise cause of sudden death in coronary heart disease has not yet been entirely clarified, the available evidence permits the medical field to ascribe death in the majority of these cases to a grave disturbance in cardiac electrical activity resulting in ventricular fibrillation.

While it is not possible to predict with unerring exactness which patient suffering from coronary heart disease will be the victim of sudden death, several high risk groups of patients can be recognized. For example, patients who have experienced myocardial infarction, even though they may be surviving in good health, run a substantial risk of dying suddenly, a risk several times greater than that associated with the general population. Further, if patients with myocardial infarction have a history of serious ventricular arrhythmias and-/or of cardiac arrest, or if evidence of persistent myocardial irritability is present, it may be logically assumed that the risk of sudden death is increased substantially. Patients like those described above would greatly benefit from an automatic, standby or demand defibrillator.

Another recognizable class of patients particularly in need of an automatic defibrillator is the class composed of those who have not shown prior histories of myocardial infarction but who show severe symptoms of coronary heart disease, such as ventricular arrhythmias resistant to medical treatment or angina pectoris.

Finally, there are scores of individuals walking the streets today who experience recurring episodes of atrial fibrillation, atrial flutter, or tachycardia. While not life-threatening, these supra-ventricular arrhythmias can become debiliting and lead to complications, and hence require treatment when present. Such individuals require frequent electrical or pharmacological conversion under the care of their physicians to return their hearts to normal sinus rhythm.

Great strides are presently being made to develop an automatic, fully implantable ventricular defibrillator. See, for example, U.S. Pat. Nos. Re. 27,652 and 27,757, where the first concept of the automatic implantable ventricular defibrillator is described. Recent advances have also been made in enhancing the reliability of fibrillation detectors. In this latter regard, see copending U.S. Pat. Applications Ser. Nos. 878,005 and 878,006, each filed on Feb. 15, 1978. Furthermore, as outlined in copending U.S. Pat. Application Ser. No. 801,300, filed on May 27, 1977, steps have been taken to improve the reliability of the implanted defibrillator by the provision of circuitry which interrogates the implanted electronics to verify proper operation before a defibrillating shock is delivered.

Notwithstanding the substantial steps which have been taken to develop the automatic, fully implantable defibrillator and to ensure the operation of the sensing and defibrillating circuitry, it must not be forgotten that the implantable defibrillator is in its infancy. Accordingly, there is a current need for data which either verifies the accuracy or which uncovers the failings of the sensing and defibrillating circuits. Specifically, there is a need for a practical device capable of providing data by recording and subsequently reproducing desired portions of an electrocardiogram (ECG) signal produced by a heart prior to and during the occurrence of various disturbances in cardiac electrical activity. With such a device, not only could the operation of the implanted defibrillator be verified, but valuable information about the patient's heart activity prior to and during cardiac arrhythmias could be obtained. Furthermore, there is a need for a practical device which could be worn by a patient to monitor heart activity even in the absence of an implanted defibrillator.

It is toward the object of meeting the foregoing needs that the present invention is directed.

SUMMARY OF THE INVENTION

The subject invention relates in general to a device for recording and subsequently reproducing desired portions of an ECG signal produced by a heart prior to and during the occurrence of various disturbances in cardiac electrical activity. Through the use of an appropriate transducer, the electrical activity of a patient's heart is detected and converted into a typical ECG signal.

More specifically, in the first (implanted) embodiment of the subject invention, the ECG signal is converted to a convenient digital form. The digital signal representing the ECG signal is stored on a FIFO (first in, first out) basis in a first memory having a predetermined small capacity. A fibrillation detector which continuously monitors the ECG signal produces a fibrillation detected logic signal at some time after the onset of a fibrillation episode. Circuitry is provided to cause the first memory to stop storig the digital representation of the ECG signal and to hold the previously stored ECG signal when this logic signal occurs. A second, large capacity memory is made operative in response to the fibrillation detected logic signal, and is provided for storing subsequent ECG signals for an extended period of time.

In addition, circuitry is provided for reading out the data stored in the first memory, the data representing heart action taking place prior to the fibrillation episode, and for reading out data from the second memory, the data representing heart action taking place during and subsequent to the fibrillation episode. Usually the readout operation is performed by a physician or assistant at the physician's office or at a hospital in conjunction with a display for subsequent interpretation.

In the second (external) embodiment of the present invention, the means used to sense the heart's cardiac electrical activity as an ECG signal takes the form of chest electrodes placed on the anterior chest wall of the patient. Conventional telemetry techniques are used to broadcast the ECG signal from the patient. This signal is received for recording and subsequent playback by the circuitry of the subject invention, which is housed in a convenient container such as a briefcase. In this embodiment, the received ECG signal is converted to a convenient digital form. The digital signal representing the ECG signal is stored on a FIFO basis in a storage device having a predetermined capacity. An arrhythmia detector which continuously monitors the received ECG signals produces an arrhythmia detected logic signal at the occurrence of a disturbance in cardiac electrical activity. By way of example, such a disturbance may be produced by ventricular tachycardia, bradycardia, asystole, ventricular flutter, ventricular fibrillation, and ectopic beats. The arrhythmia detected logic signal turns on a tape recorder which records the output of the storage device. After the disturbance has ceased and the heart has returned to normal cardiac electrical activity the arrhythmia detected logic signal ceases. The recorder continues to record the output of the storage device for a predetermined time period equal, for example, to the time interval necessary for the storage device to once read out its entire contents. After this has taken place the recorder shuts down. Thus the recorder now possesses on a magnetic tape in digital form, the desired portion of the received ECG signal produced by the heart prior to and during the occurrence of the disturbance in cardiac electrical activity.

The tape is played back by a physician or trained assistant at the physician's office or at a hospital in conjunction with a display device for subsequent interpretation.

Customarily, the term electrocardiogram (ECG) implies the use of electrodes on the body surface to obtain electrical signals indicative of heart activity. The term electrogram, on the other hand, generally refers to measurements made at the surface of the heart. As used herein, "ECG" is defined broadly, and refers to any measurement of the electrical activity of the heart, notwithstanding the source or technique of the measurement.

It is accordingly an object of the present invention to provide a device for recording and subsequently reproducing desired portions of an ECG produced by a heart prior to and during the occurrence of a disturbance in cardiac electrical activity.

It is another object of the present invention to provide a low power implantable device for preserving valuable information about the patient's heart activity as represented by an ECG signal occuring prior to and during a fibrillation episode.

It is still another object of the present invention to provide a lightweight, external device employing radio telemetry techniques for recording and subsequently reproducing a desired portion of an ECG signal produced by a heart prior to and during the occurrence of a disturbance in cardiac electrical activity.

It is yet another object of the present invention to provide a low power implantable device for recording and subsequently reproducing portions of ECG signals relating to multiple fibrillation episodes as experienced by a patient.

It is a further object of the present invention to provide a lightweight external device for recording and subsequently reproducing portions of ECG signals relating to multiple disturbances in cardiac electrical activity as experience by a patient.

It is yet a further object of the present invention to provide a device for recording and subsequently reproducing information pertinent to a defibrillation attempt by an implantable defibrillator.

It is yet another object of the present invention to provide treatment verification capabilities as part of an automatic implantable defibrillator, which has a device for storing and discharging defibrillating energy through the heart of a wearer and a device for charging the storage and discharge device upon detection of fibrillation.

It is still another object of the present invention to provide a device which will aid in recognizing the need for a fully implantable ventricular defibrillator in a patient suffering from coronary heart disease.

It is yet another object of the present invention to provide a device which will aid in treatment of patients suffering from cardiac arrhythmias.

It is still a further object of the present invention to provide a device for verifying the operation of an implanted defibrillator.

Other objects and advantages of this invention will further become apparent hereinafter and in the drawings, in which:

DESCRIPTION OF THE PREFERRED EMBODIMENTS

In describing the preferred embodiments of the invention illustrated in the drawings, specific terminology will be resorted to for the sake of clarity. However, it is not intended to be limited to the specific terms so selected, and it is to be understood that each specific term includes all technical equivalents which operate in a similar manner to accomplish a similar purpose.

Figure 1:
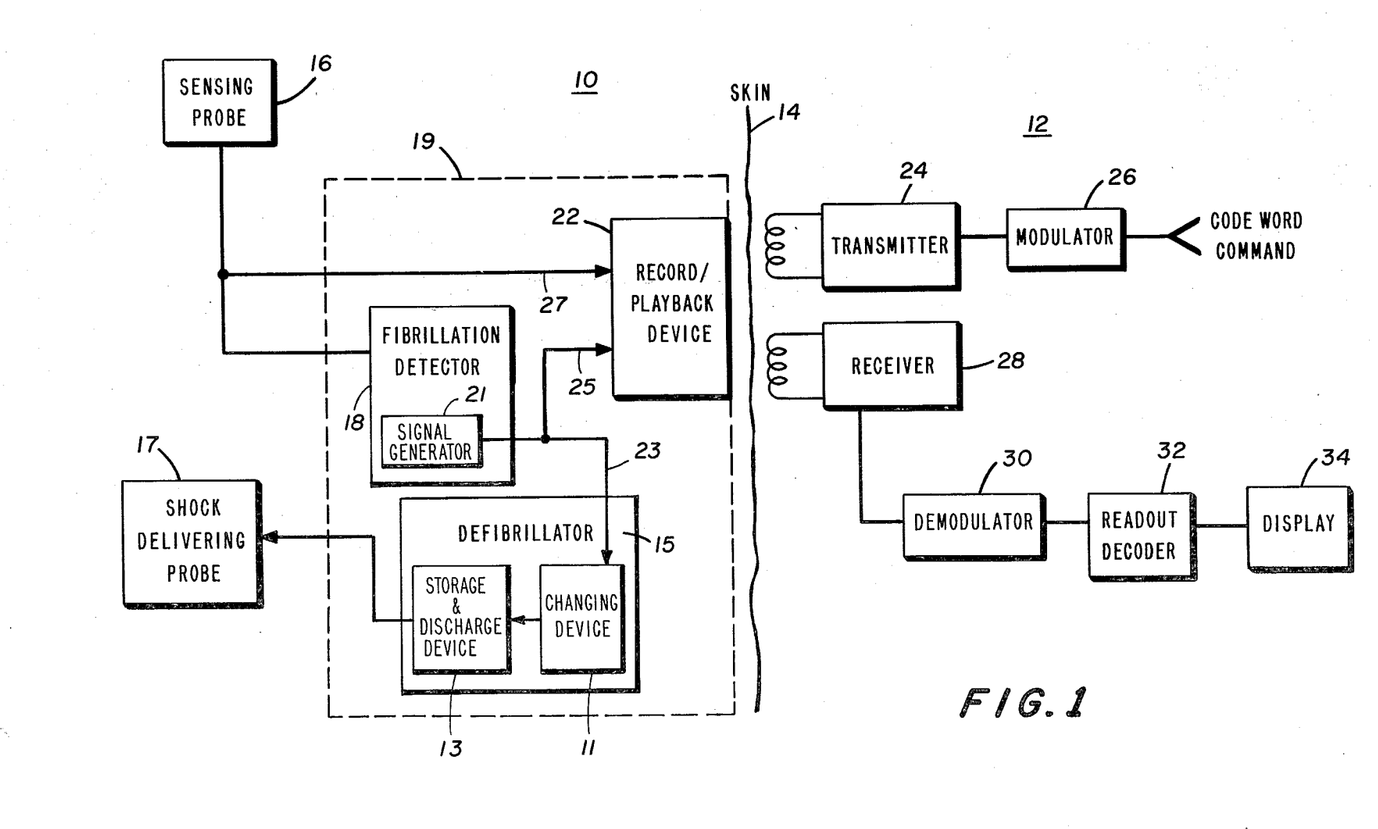
FIG. 1 is a general block diagram of a preferred embodiment of the subject invention.

The first embodiment of the subject invention will be described in general with reference to FIG. 1. A portion of the device implanted within a patient is indicated generally at 10 and is adapted to associate with an external portion of the device generally designated at 12. The numeral 14 schematically represents the skin of the patient and hence shows the separation between the implanted device 10 and the external device 12.

A sensing probe 16 senses the heart's cardiac electrical activity as an electrocardiogram (ECG) signal. This signal is received by a fibrillation detector 18, which includes a signal generator 21 that issues a fibrillation detected (FD) signal. A record/playback device 22 also receives the ECG signal from the probe 16 on line 27 along with a fibrillation detected (FD) signal from the fibrillation detector 18 on line 25. A defibrillator 15 also receives the FD signal from the fibrillation detector 18, on line 23. The defibrillator 15 is of conventional design and includes a storage and discharge device 13 for storing and discharging defibrillating energy through the heart of a wearer, and a charging device 11 for charging the storage and discharge device upon receipt of the FD signal on line 23. When a fibrillation is detected the defibrillator issues a defibrillating shock to the heart via a shock delivering probe 17. In this embodiment the defibrillator 15, the fibrillation detector 18, and the record/playback device are encased in the same implantable housing 19. The record/playback device 22 records a desired portion of the ECG signal produced by the heart prior to and during a fibrillation episode.

The information stored in the record/playback device 22 may be retrieved and converted to an eye-readable form for subsequent examination through the use of the external device 12. A code word command is transmitted to the record/playback device 22 through a transmitter 24 via a modulator 26. The information stored in the record/playback device is received by receiver 28. The output of receiver 28 passes through a demodulator 30. The output of the demodulator is fed to a display device 34 via a readout decoder 32 to display the information stored in the record/playback device in an eye-readable format.

Figure 3:
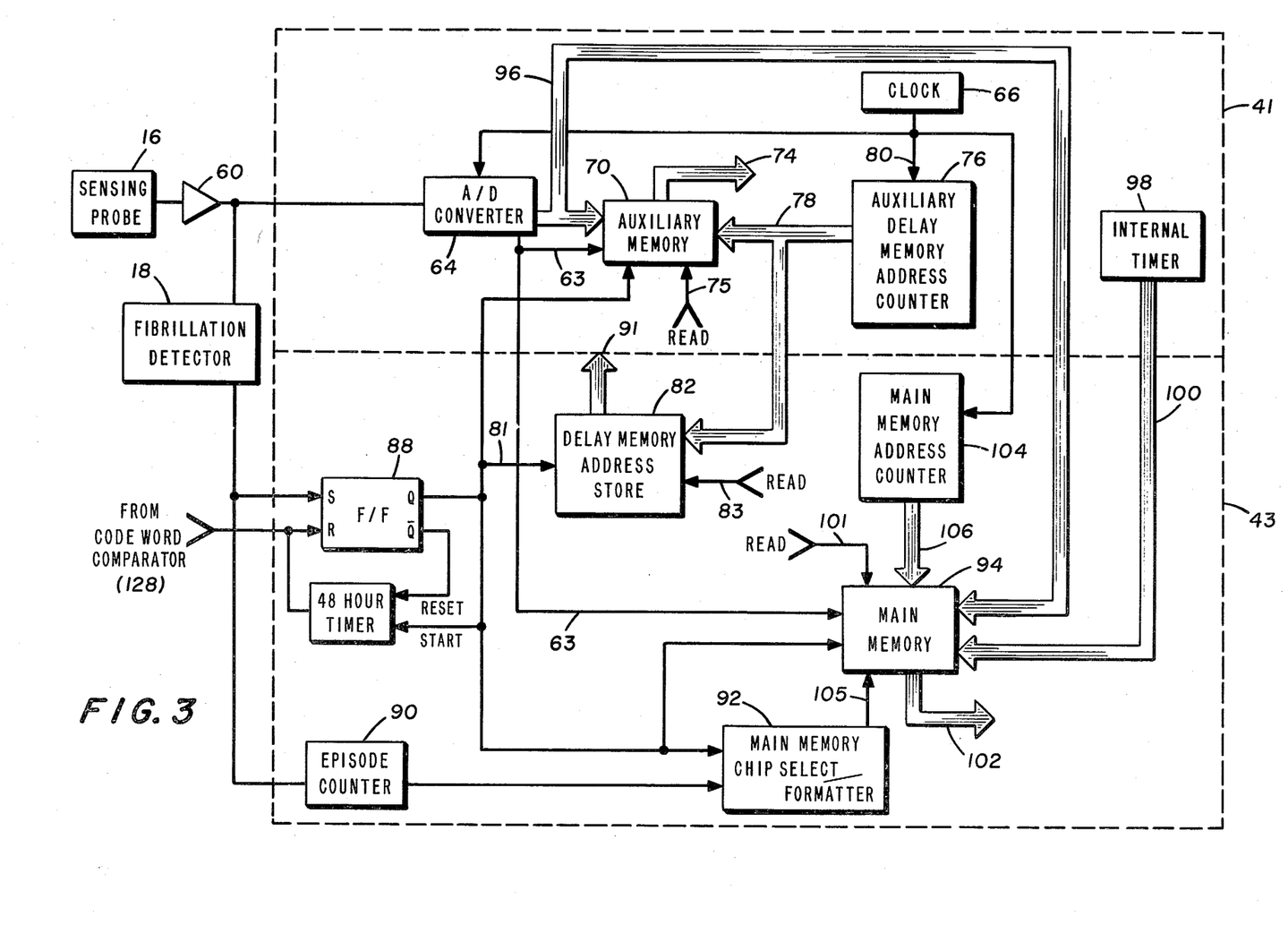
FIG. 3 is a detailed block diagram of the recording or storing portion associated with the FIG. 1 embodiment.

How the desired portion of the ECG signal produced by a heart prior to and during a fibrillation episode is recorded or stored may be explained with reference to FIG. 3.

The sensing probe 16 provides an ECG signal. This signal is amplified through an amplifier 60 and fed into a fibrillation detector 18. The fibrillation detector is preferably of the type disclosed in copending U.S. Application Ser. No. 878,006. The output of the amplifier 60 is also fed to an analog-to-digital (A/D) converter 64, which converts the ECG signal into a digital representation. The digital representation is made up of a series of words wherein each word contains four to six bits (hereinafter four for convenience). A clock 66 provides an INITIATE CONVERSION signal as well as gating pulses to the A/D converter 64 via lines 68. The digital output of the A/D converter is written into an auxiliary delay memory, or storage device 70 by a WRITE strobe produced by the A/D converter on lines 63 when conversion has been completed. In the preferred embodiment the auxiliary memory 70 contains a 4K (assuming a four bit word) random access memory (RAM). In order to operate with the lowest possible power dissipation the RAM is of the complementary metal oxide semi-conductor (CMOS) type. As stated before each word of digital data contains 4 bits. Thus the auxiliary memory has the capacity to store 1,024 words or 4,096 bits of digital information. The auxiliary memory also contains the usual read/write control circuitry for writing information into the RAM and for reading information out of the RAM. The auxiliary memory also contains the usual row and column decode circuitry for addressing a currently selected memory location for reading or writing. Stored data is read out of the auxiliary memory onto a data bus 74 in response to a READ signal received on lines 75. How the READ signal is provided will be explained in detail hereinafter. An auxilliary memory address (AMA) counter 76 provides a 10-bit address word to the auxiliary memory on address bus 78. The clock 66 applies clock pulses on lines 80 to increment the AMA counter 76. The AMA counter 76 provides address data to sequentially address all of the RAM locations in the auxiliary memory. As long as clock pulses are received on lines 80, the AMA counter will continously repeat the address sequence.

The address data is also received by an auxiliary memory address (AMA) store 82 via the address bus 78. In this way the address of the currently selected word in the auxiliary memory is presented to the AMA store. The AMA store 76 may be any conventional storage device which is capable of storing an address from the address bus 78 in response to a WRITE signal and which is capable of reading out the stored address in response to a READ signal. In addition the AMA store could be a dedicated portion of the auxiliary memory 70, or the main memory 94. The address stored is read from the AMA store on store bus 91. The AMA store receives such a WRITE signal on lines 81 and such a READ signal on lines 83. How these signals are produced will be explained in detail hereinafter.

The output of the fibrillation detector 18 is fed to the set input of a bistable flip-flop 88 and to an episode counter 90. The Q output of flip-flop 88 is fed to the start input of a 48-hour timer 92. The Q output of flip-flop 88 is fed to a reset input of the 48-hour timer. The 48-hour timer may be either a count-up or count-down counter. When 48 hours has passed the timer produces an output signal which is fed to the reset input of flip-flop 88.

The Q output of flip-flop 88 is also fed to the auxiliary memory 70, to AMA store 82, and to a main memory chip selector/formatter 92. How the Q output affects these three elements will be explained hereinafter with reference to the operation of the subject invention.

A main memory or storage device 94, which contains a plurality of RAM chips, receives data from the A/D converter 64 via the data bus 96. The number and capacity of the RAM chips is determined by the amount of information desired to be stored. In a preferred embodiment there are three 4K RAM chips. The main memory 94 also receives data from an internal timer 98 on time bus 100. The internal timer, which as an example may be a digital watch chip, provides a continuous read out of desired information such as time and date in the form of a digital signal referred to as a time tag. Data is read from the main memory onto data bus 102 in response to a READ signal received on lines 101. How the READ signal is provided will be explained in detail hereinafter. A main memory address (MMA) counter 104 provides address data on address bus 106 to sequentially address the word locations in the main memory in the same way as the AMA counter 76. Alternatively, the AMA counter can be used to address the main memory if the counter is cleared just after the pointer to the last word in the auxiliary memory is strobed into the AMA store, all as discussed in detail in the description of FIGS. 3 and 4.

The selector/formatter 92 is responsive to the Q output of flip-flop 88 and the output of episode counter 90. The selector/formatter is used to select and enable a particular RAM chip in the main memory. The selector/formatter counts the number of words in the chip selected. When the selector/formatter determines that the chip is full it disables that chip and selects and enables another chip.

In order to keep power dissipation to a minimum, only the auxiliary memory 70, the A/D converter 64, the clock 66, the AMA counter 76, and the time clock 98 are continuously powered. These elements are enclosed within the dotted line 41. The remaining elements enclosed within the dotted line 43 are powered, and thereby made operative, only after the issuance of a fibrillation detected signal from the fibrillation detector 18.

Figure 4:
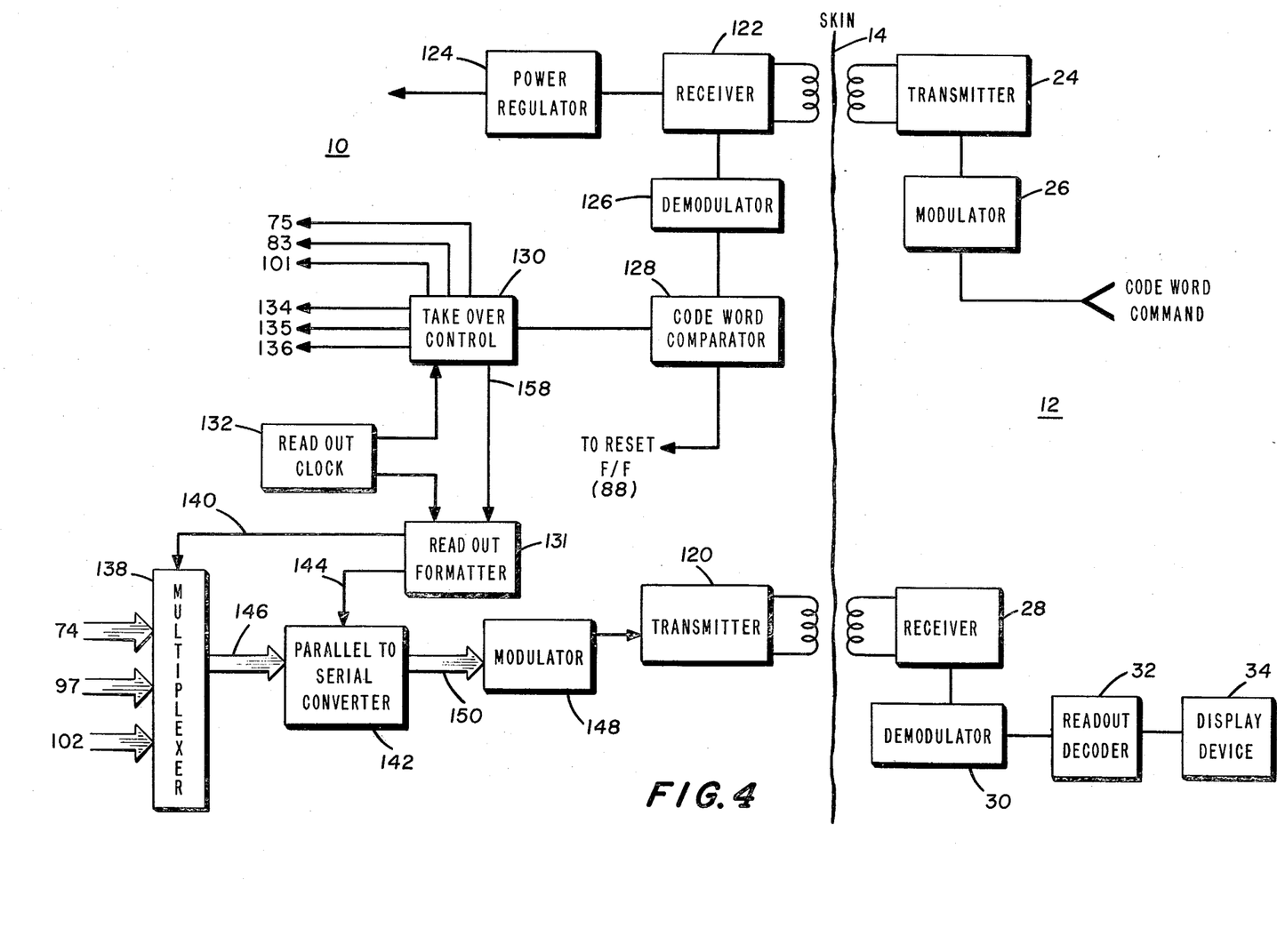
FIG. 4 is a detailed block diagram of the reproducing or retrieving portion association with the FIG. 1 embodiment.

The elements used to configure the reproduction or data retrieval circuitry of the embodiment shown in FIG. 1 will be explained with reference to FIG. 4. As previously mentioned, the portion of the device generally designated as 10 is implanted within the patient and the device generally designated at 12 is external to the patient. A transmitter 120 and a receiver 122 are located near to but below the skin 14 of the patient. A receiver 28 and a transmitter 24 are located external to the patient. Power and information signals are transmitted by telemetry through the skin of the patient by way of transmitter 24 and receiver 122 as well as receiver 28 and transmitter 120. This type of information transfer is well known in the art and operates under the principle of transformer coupling between primary and secondary windings. When any one of the transmitters is activated a signal is transformer coupled across the skin of the patient. This signal is received through the secondary winding of the coupling transformer at the associated receiver.

A code word command to initiate retrieval is fed into a modulator 26. The output of the modulator 26 is fed into the transmitter 24. The output of the transmitter 24 is received by the receiver 122 which produces two output signals, one of which is used to activate a power regulator 124 and the other of which is fed to a demodulator 126. The output of the demodulator is fed to a code word comparator 128. The code word comparator produces two output signals. The first signal is fed to take-over control 130. The second signal is fed to the reset input of flip-flop 88. A read-out clock 132 provides timing signals to the take-over control 130. The take-over control 130 provides control signals to the AMA counter 76 on lines 134, to the selector/formatter on lines 135 and to the MMA counter 104 on lines 136. The take-over control 130 also provides READ commands to the auxiliary memory 70 on lines 75, to the main memory 94 on lines 101, and to the AMA store 82, on lines 83. A readout formatter 131 receives an enabling signal from the take over control 130 via lines 158. The read-out clock 132 provides timing signals for the read-out formatter 131. The readout formatter, which will be explained in greater detail hereinafter, provides control signals to a multiplexer 138 on lines 140, and to a parallel-to-serial (P/S) converter 142 on lines 144. The multiplexer 138 receives data from the auxiliary memory via data bus 74, from the main memory via data bus 102, from the AMA store via store bus 91. The multiplexer produces a parallel data stream on lines 146. This data stream is converted to a serial data stream by the P/S converter 142. The serial data stream is fed into a modulator 148 on data lines 150. The output of the modulator is fed to the transmitter 120. The output of the transmitter is received by receiver 28 and is demodulated by a demodulator 30. The output of the demodulator 30 is fed to a display device 34 via a readout decoder 32, which will be described in greater detail hereinafter. The display device 34 provides in eye-readable format the desired portion of the ECG signal produced by the heart prior to and during a fibrillation episode.

The operation of the fibrillation episode recording and reproducing device will now be described with reference to FIGS. 3 and 4. As previously explained, the ECG signal sensed by the probe 16 passes through amplifier 60, into the A/D converter 64, to emerge therefrom as a series of four bit data words. These words are stored in the auxiliary memory 70 at locations determined by the address commands from the auxiliary memory address counter 76. Conversion is initiated and carried out in the A/D coverter 64 in response to pulses from the clock 66. When conversion is complete, the A/D converter products a WRITE strobe on lines 63. Thus, data from the A/D converter is written into the auxiliary memory via data bus 96. After the entire memory has been addressed the memory address counter starts the address sequence over again and new digital data from the A/D converter is written into the memory locations of the auxiliary memory 70. New digital data replaces previously stored digital data on a first in, first out (FIFO) basis. In the preferred embodiment, the 4K RAM is capable of storing 1,024 words of digital data. These 1,024 words represent the most recent 10 seconds (assuming a sampling rate of 100 Hz) of ventricular heart muscle contractions as sensed by the probe 16. Thus at any time 10 seconds of the most recent ECG signal may be stored in digital form within the auxiliary memory 70. It should be pointed out that the memory capacity may be increased or decreased in order to store data produced during a greater or lesser time period.

When fibrillation is sensed, the fibrillator detector 18 produces an output signal which sets flip-flop 88. In addition, the episode counter 90 registers the first episode in response to the fibrillation detector output signal. Since flip-flip 88 is bi-stable the Q output remains high when the flip-flop is set. The Q output starts the 48-hour timer 92. The Q output also provides a WRITE DISABLE command to the auxiliary memory 70 causing it to stop updating and to hold the data words already stored. The A/D converter 64 and the AMA counter 76 are not affected by the WRITE DISABLE signal. The Q output also provides a WRITE command to the AMA store 82. The AMA store 82 responds by storing the address of the last word placed into the auxiliary memory 70 at the time the WRITE DISABLE command was received by the delay memory. The address word is received by the AMA store 82 from the AMA counter 76 via the address bus 78. The memory address stored in the AMA store 82 will point to a specific location in the auxiliary memory 70; it is important to know the address of that location. In this manner, when the data is read from the chip, the address will provide a reference point to enable a sequential reconstruction of the stored data.

The Q output is also used to provide power to the main memory 94 and the chip selector/formatter 92. In the preferred embodiment the main memory contains 3 RAM chips each having a 1,024 4-bit word capacity. In response to the signal from the episode counter 90 the selector/formatter 92 provides an ENABLE signal to the main memory 94 via lines 105 to allow a first selected chip to accept data. The MMA counter 104 is started from zero, and supplies addresses to the main memory.

The A/D converter produces a WRITE strobe on lines 63 in the manner described hereinbefore. The selected chip in the main memory 94 responds by storing data from the A/D converter 64 via the data bus 96. The selector/formatter 92 contains an internal counter for keeping track of the number of words written into the selected chip. When the selector/formatter 92 determines that the first selected chip is full, it disables that chip. This causes the first selected chip to refuse any additional data and to hold the data already stored therein. At the same time the selector/formatter enables the second selected chip, which operates in the same way as the first selected chip. The second selected chip stores data from the A/D converter 64 in response to the WRITE strobe issued by the A/D converter.

The selector/formatter 92 keeps track of the number of words written into the second selected chip in the same way it did for the first selected chip. When the selector/formatter 92 determines that the second selected chip is full it disables that chip. This causes the second selected chip to refuse any additional data and to hold the data already stored therein. If additional chips are present in the main memory 94, they will be handled in the same manner as described hereinbefore with respect to the first and second selected chips. Such additional chips can be used to record the results of any subsequent defibrillation attempts, should the first on subsequent defibrillation attempt be unsuccessful. In any event, a certain number of bit locations in the main memory are reserved to receive the time tag from the internal timer 98. The time tag is inserted into the main memory 94 when the other portions of the main memory are full.

At this point, it may be helpful to summarize what has taken place. A fibrillation episode has been detected. The auxiliary memory 70 has been disenabled and holds digital data representing the most recent portion of the ECG signal sensed by the probe 16 just prior to the onset of the fibrillation episode. The address of the last word placed into the auxiliary memory 70 has been stored in the AMA store 82. The main memory 94 has been enabled and is storing digital data representing the portion of the ECG signal sensed by the probe 16 after the onset of the fibrillation episode.

How the data stored in the auxiliary memory 70, the main memory 94 and the AMA store 82 is retrieved and read out in the preferred embodiment of the subject invention will now be described with reference to FIGS. 3 and 4.

To initiate readout of the data stored in the auxiliary memory and the main memory, a code word command is transmitted by transmitter 24 after passing through modulator 26. The code word command may be a digital word of any desired length. The transmitted signal is received by receiver 122. One of the outputs of the receiver 122 is used to activate a power regulator 124, which may be used to supplement or replace the power supplied to operate the fibrillation episode recording and reproducing device. Another signal from the receiver 122 is fed into a code word comparator 128. The comparator comprises a series of logic gates configured to determine the truth of the transmitted code word command. If the code word command is a true one, the take-over control 130 becomes operative in response to a signal from the comparator 128.

The take-over control 130 operates at a rate determined by the read-out clock 132. Control signals are provided to the AMA counter 76 by the take-over control 130 via lines 134. These control signals cause the AMA counter to produce address data at a much higher rate than the counter produced in response to the pulses from clock 66. Control signals are provided to the AMA counter 104 via lines 136 with the same results. The take-over control also provides READ commands to the auxiliary memory 70 via lines 75, to the main memory 94 via lines 101, and to the store 82 via lines 83. A control signal is provided by the take-over control via lines 135 to enable the selector/formatter 92. In response to all of these control signals, the data stored in the auxiliary memory 70 is read onto data bus 74, the data stored in the main memory 94 is read onto data bus 102, and the address stored in the AMA counter 82 is read onto store bus 91. A multiplexer 138 contains a sufficient number of inputs for receiving all of the digital information being transported on the aforesaid buses. The multiplexer also contains a desired number of outputs from which the multiplexed data is issued. The readout formatter 160 contains a logic array to provide a recurring sequence of address codes to the multiplexer on lines 140. The address codes determine the manner in which the digital information is routed from the multiplexer inputs to the multiplexer outputs. The rate at which the address codes are provided is determined by the output of the readout clock 132. The readout formatter is made operative by an enabling signal from the take over control 130 via lines 158.

The multiplexer 138 under the control of the readout formatter 160 multiplexes the incoming digital information to produce a parallel data stream on lines 146. The parallel-to-serial converter 142 is made operative by an ENABLE signal and PARALLEL/SERIAL CONVERT signals received from the readout formatter on lines 144. The parallel data stream on lines 146 is converted by the P/S converter to a serial data stream appearing on lines 150. The serial data is fed into the modulator 148 and then into the transmitter 120. The transmitted signal is received by receiver 28 and fed into the demodulator 30. Thus it can be seen that the output of the demodulator 30 is the serial data stream which was fed into the modulator 148. The output of the demodulator is fed to a display device 34 via a readout decoder 32. The readout decoder 32 contains a logic array for converting the serial data stream into a series of driving signals for the display device 34. The logic array of the readout decoder is chosen to take into account the order in which the multiplexer 138 and the P/S converter 142 formatted the serial data stream. The display device 34 shows in eye-readable format the desired portion of the ECG signal produced by the heart prior to and during the fibrillation episode.

If it is desired to record more than one fibrillation episode, the episode counter 90 may be configured to produce a discrete signal for each episode to be recorded. The selector/formatter 92 would respond by enabling a selected portion of the main memory 94. Th digitized portion of the ECG signal associated with a particular episode would then be stored in the selected portion of the main memory.

Returning now to the 48-hour timer 92, if the data stored in the delay memory 70 and the main memory 94 is not extracted from these locations within a 48-hour time period, the timer 92 produces a signal which acts to reset the flip-flop 88. In this way, Q goes low and Q goes high. When Q goes low, the WRITE DISABLE command is removed from the delay memory 20, the WRITE command is removed from the AMA store 82, power is removed from the main memory 94 causing it to dump its contents, and the selector/formatter 92 is inactivated.

Figure 2:
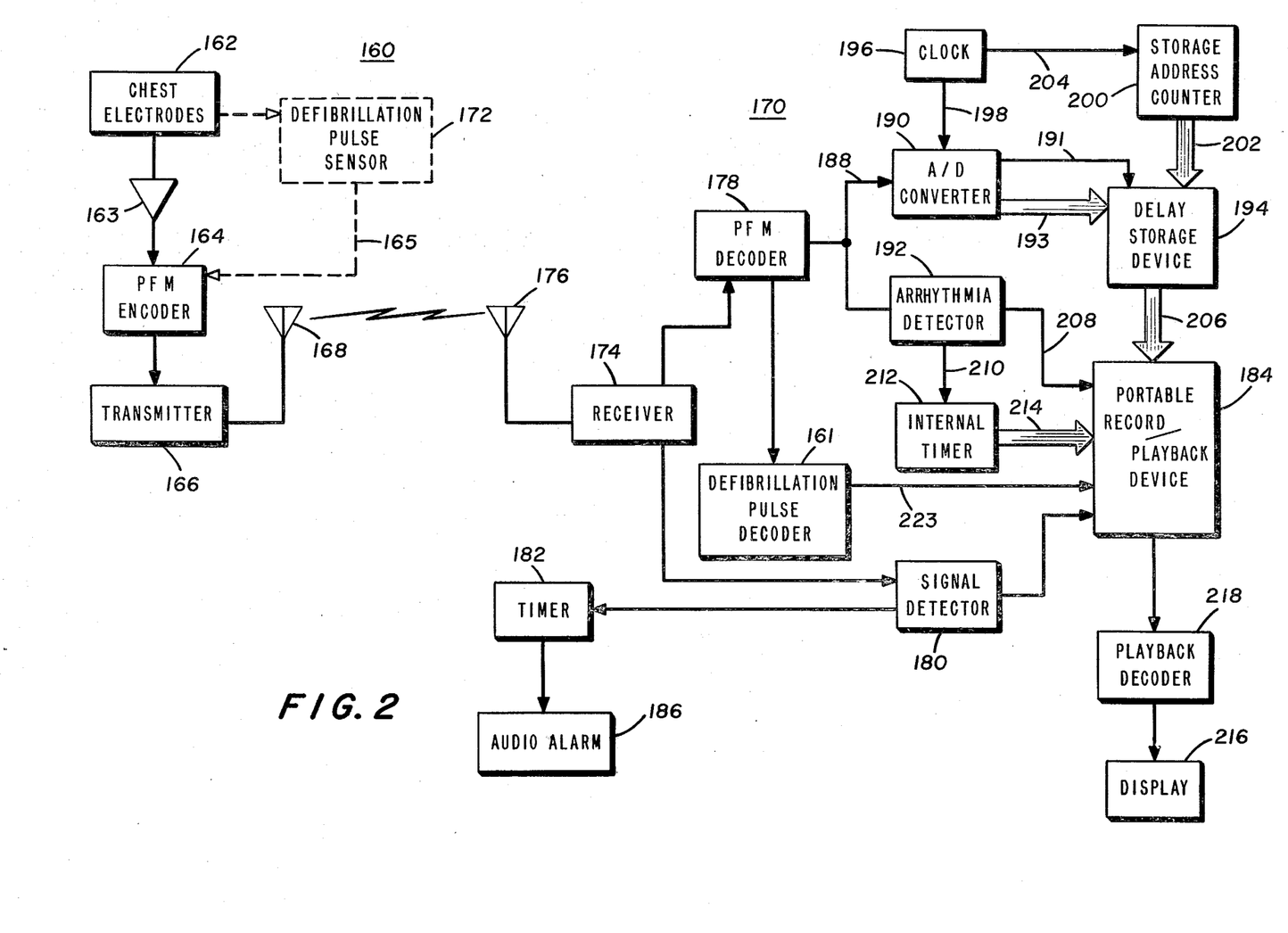
FIG. 2 is a detailed block diagram of another preferred embodiment of the subject invention.

Another embodiment of the subject invention will now be described with reference to FIG. 2. The device comprises two units generally designated as 160 and 170. The first unit 160 is an ECG signal transmission unit which is worn by a patient. The second unit 170 is an ECG signal receiving and processing unit, is designed to be located at some defined distance from the patient, and is housed in a convenient container such as a briefcase.

Chest electrodes 162 placed on the anterior chest wall of the patient sense the heart's cardiac electrical activity as an ECG signal, which is fed into an amplifier 163. A pulse frequency modulation (PFM) encoder 164 converts the amplified ECG signal into a PFM waveform. In this regard, the PFM waveform includes a plurality of uniform width pulses, the spacing (or frequency) of which represents the data being transmitted. The PFM waveform is fed to a transmitter 166, the output of which is fed to an antenna 168. If the patient has an implanted defibrillator, a defibrillation pulse sensor 172 shown in phantom, is included in the unit 160. The defibrillation pulse sensor receives the ECG signal from the chest electrodes. A normal ECG signal has a magnitude of approximately 1 millivolt while a cardioverting or defibrillating shock has a magnitude of approximately 10 volts measured at the skin. Thus, when the implanted defibrillator issues a cardioverting shock, the sensor 172 detects the cardioverting shock and issues a signal which is fed into the PFM encoder for PFM encoding and subsequent transmission by the transmitter 166 and antenna 168. At the same time, the signal from the sensor 172, via line 165, causes the PFM encoder 164 to provide a special signal to the transmittter indicative of the delivery of a defibrillating pulse.

A receiver 174 receives the transmitted PFM waveform via an antenna 176. The output of the receiver is fed to a pulse frequency modulation (PFM) decoder 178 and also to a signal detector 180. When the output of the receiver 174 drops below a certain level, or the demodulated pulses are not of the correct (transmitted) width, the signal detector produces an enabling signal which is fed to a timer 182 and a disabling signal which is fed to a portable record/playback (R/P) device 184 such as a casette recorder or the like. The timer 182 produces a signal of desired duration to activate an audio alarm 186. In this way the patient is made aware of any interruption in the transmission of ECG signals by the unit 160, or in the reception of ECG signals by the unit 170, or that he/she has entered an area of electromagnetic interference (pulse width not as transmitted). The patient is also alerted to the fact that he/she has placed the unit 160 out of the reception range of the unit 170.

The PFM decoder 178 decodes the PFM waveform received from the receiver 174 to reconstruct the ECG signal. The reconstructed ECG signal, appearing on lines 188, is fed to an analog-to-digital (A/D) converter 190, wherein the ECG signal is converted into a digital representation. The digital representation is made up of a series of words wherein each work contains eight bits. The reconstructed ECG signal, appearing on lines 188, is also fed to an arrhythmia detector 192. A particular embodiment of the arrhythmia detector will be described in greater detail hereinafter. The output of the A/D converter 190 is received and stored on a FIFO basis in a delay storage device 194 having a predetermined capacity. The storage device 194 may contain either a random access memory (RAM), or shift registers.

In one embodiment, the storage device 194 contains an 8K random access memory, which is capable of storing 1,024 words of digital data. These 1,024 words represent the most recent 10 seconds of cardiac electrical activity as sensed by the chest electrodes 162. Thus at any time, 10 seconds of the most recent ECG signal may be stored in digital form within the storage device 194. It should be pointed out that the storage capacity may be increased or decreased in order to store data produced during a greater or lesser time period.

A clock 196 provides an initiate conversion signal as well as gating pulses to the A/D converter via lines 198. A storage address (SA) counter 200 provides address codes to the storage device 194 via lines 202. The clock 196 supplies clock pulses on lines 204 to increment the SA counter. The SA counter provides address codes to a sequentially address all of the storage locations in the storage device. As long as clock pulses are received on lines 204, the SA counter will continuously repeat the address sequence.

In operation, the output of the A/D converter 190 is stored in the storage device at locations determined by the address codes from the SA counter 200. Conversion is initiated and carried out in the A/D converter in response to pulses from the clock 196. When conversion is complete, the A/D converter produces a WRITE strobe on lines 191. Thus, data from the A/D converter is written into the storage device via data bus 193. After the entire RAM has been addressed, the SA counter starts the address sequence over again and new digital data from the A/D converter is written into the storage locations of the storage device 194, on a first in, first out (FIFO) basis. The storage device 194 contains read circuitry for continuously reading out the replaced digital data onto lines 206.

In another embodiment, the storage device 194 is implemented through the use of eight 1,024-bit shift registers. In this embodiment, the storage address counter 200 is not needed. As stated before, the digital representation from the A/D converter 190 is made up of a series of words wherein each contains eight bits. The eight bits of each word are written into the first stages of the shift registers, one bit into each register, by the WRITE strobe on lines 191. The data within each shift register is sequentially shifted under the control of the clock 196. Eventually, the data is shifted to the last stage of each shift register. The data in the last stage of each shift register is shifted out onto lines 206 as a series of eight bit words. In this way new digital data replaces previously stored digital data on a first in, first out (FIFO) basis.

When the arrhythmia detector 192 detects a disturbance in cardiac electrical activity, it issues two signals, one on lines 208 and one on lines 210. The signal on lines 208 enables the record/playback device 184. The signal on lines 210 is fed to an internal timer 212, which as an example may be a digital watch chip. The internal timer continuously keeps track of desired information such as time and date in the form of a digital signal referred to as a time tag. The signal on lines 210 causes the internal timer 212 to issue a time tag on lines 214.

The record/playback device 184 in response to the enabling signal records on a magnetic tape the time tag and the digital data appearing on lines 206. After the disturbance has ceased and the heart has returned to normal cardiac electrical activity, the enabling signal on lines 208 ceases. The record/playback device continues to record the output of the storage device 194 for a predetermined time period equal, for example, to the time interval necessary for the storage device to once read out its entire contents. After this has taken place, the recorder shuts down. Thus the recorder now possesses on the magnetic tape in digital form, the desired portion of the ECG signal produced by the heart prior to and during the occurrence of the disturbance in cardiac electrical activity.

Any subsequent disturbances in cardiac electrical activity are recorded in the same manner as previously described. In each case, the record/playback device 184 in response to the enabling signal, records on the magnetic tape the time tag and the digital data appearing on lines 206. The capacity of the record/playback device is determined by the length of the magnetic tape and the speed at which a recording is made.

The defibrillation pulse sensor 172 is used in the embodiment of the invention when a patient has an implanted defibrillator. As stated previously, a normal ECG signal has a magnitude of approximately 1 millivolt while a defibrillating shock has a magnitude of approximately 10 volts. The defibrillation pulse sensor 172 receives the ECG signal from the chest electrodes 162 and senses the dramatic shift in pulse magnitude caused by the deliverance of a defibrillating shock. When this shift takes place, the defibrillation pulse sensor issues a defibrillation sensed (DS) signal on lines 165. The DS signal causes the pulse frequency modulation to transmit a code not normally seen during the transmission of ECG data, such as a high pulse repetition frequency. In addition, the DS signal is received by the defibrillation pulse decoder 61 after being encoded, transmitted, received, and decoded in the manner previously described with regard to ECG signals from the chest electrodes 162. The defibrillation pulse decoder 161 interprets the DS signal as an event to be recorded, and in response thereto issues the signal on lines 223 to enable the record/playback device 184 and the signal on line 210 to cause the internal timer 212 to issue a time tag.

At some point in time, the tape in the record/playback device 184 is rewound and then played back by a physician or trained assistant at the doctor's office or at a hospital. It is contemplated that the physician and the hospital will have playback equipment so that the patient is able to mail his/her cassette for interpretation. For convenience, however, the playback function is integrated with the receiving and recording functions. The information on the tape is fed to a display 216 via a playback decoder 218 to display the information in an eye-readable format for subsequent interpretation. The playback decoder 218 contains circuitry for converting the digital data on the tape into a series of driving signals for the display device 216. The circuitry of the playback decoder is chosen to take into account the order in which the record/playback device 184 has recorded the output of the storage device 194.

Figure 5:
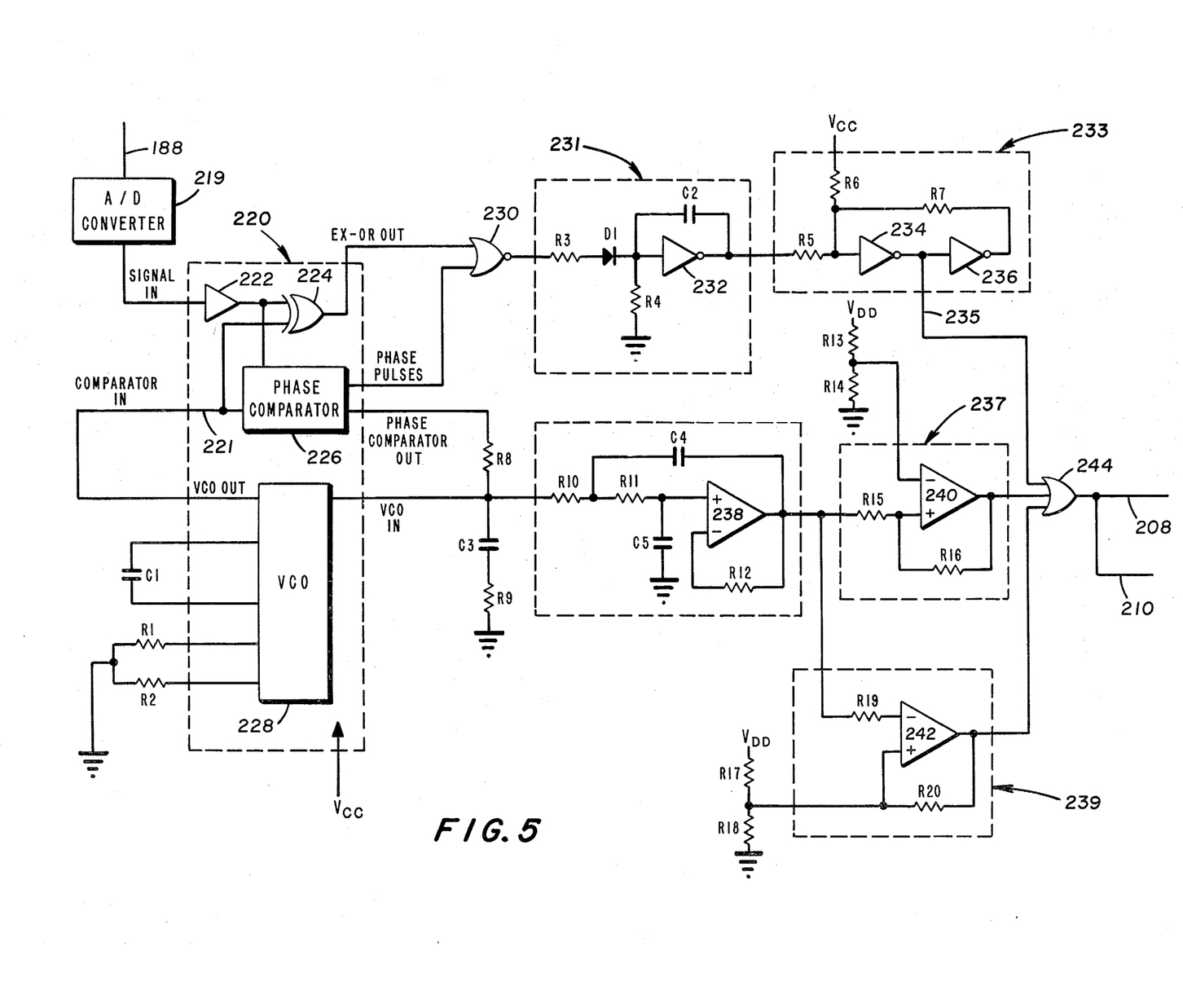
FIG. 5 is a schematic diagram of an embodiment of the arrhythmia detector associated with the FIG. 2 embodiment.

The arrhythmia detector 192 will now be described in greater detail with reference to FIG. 5. The ECG signal appearing on line 188 is fed into a phase-locked loop 220 via an A/D converter 219. One such phase-locked loop is the RCA 4046, manufactured by the RCA Corporation, Solid State Division, Somerville, New Jersey. The phase-locked loop contains an amplifier 222, the output of which is connected to one input of an exclusive-OR network 224 and to one input of a phase comparator 226. The output of a voltage-controlled oscillator (VCO) 228 is connected to the remaining input of the exclusive-OR network 224 and the remaining input of the phase comparator 226. The VCO requires an external capacitor C, and two external resistors R1 and R2. Resistor R1 and capacitor C1 determine the frequency range of the VCO and resistor R2 enables the VCO to have a frequency offset. The output of the exclusive-OR network is fed to one input of a NOR-gate 230. Phase pulses from the phase comparator 226 are fed to the remaining input of the NOR-gate 230. The output of the NOR-gate 230 is fed into the input of an inverter 232 after passing through a resistor $R_3$ in series with a diode $D_1$. A capacitor $C_2$ is connected between the input and the output of the inverter 232. One end of a resistor $R_4$ is connected to the output of inverter 232 while the other end is connected to ground. The output of inverter 232 is fed to the input of an inverter 234 after passing through a resistor $R_5$. The output of inverter 234 is fed to the input of an inverter 236 and to one input of a 3 input OR-gate 244. A resistor $R_7$ is connected between the input of inverter 234 and the output of inverter 236. A voltage Vcc, which is 6 volts D.C., is delivered to the input of inverter 234 via a resistor $R_6$.

A resistor $R_8$ is connected between the output of the phase comparator 226 and the input of the VCO 228. The input of the VCO is also connected to ground via a capacitor $C_3$ in series with a resistor $R_9$. The capacitor $C_3$ and the two resistors $R_8$ and $R_9$ from a two-pole low-pass filter to improve frequency capture range and lock-in speed. Two series resistors $R_{10}$ and $R_{11}$ are connected between the input of VCO 228 and the plus-input of an operational amplifier (op-amp) 238. The plus-input of op-amp 238 is also connected to ground via capacitor $C_5$. One end of a capacitor $C_4$ is connected to the series junction of resistors $R_{10}$ and $R_{11}$, while the other end is connected to the output of op-amp 238. A resistor $R_{12}$ is connected between the output and the minus-input of op-amp 238. The output of the op-amp 238 is fed to the plus-input of an op-amp 240 via a resistor $R_{15}$, and to the minus-input of an op-amp 242. A voltage VDD, which is 15 volts D.C., is delivered to the minus-input of op-amp 240. The minus-input of op-amp 240 is also connected to ground via a resistor $R_{14}$. A resistor $R_{16}$ is connected between the output and the minus-input of op-amp 240. The output of op-amp 240 is fed to the second input of OR-gate 244. A voltage VDD, which is 15 volts D.C., is delivered to the plus-input of op-amp 242 via a resistor $R_{17}$. The plus-input of op-amp 242 is also connected to ground via a resistor $R_{18}$. A resistor $R_{20}$ is connected between the output and the plus-input of op-amp 242. The output of op-amp 242 is fed to the third input of OR-gate 244. Finally, the output of OR-gate 244 appears on lines 208 and 210 as the detection signal.

The phase-locked loop powered by a voltage Vcc consists of a low-power, linear VCO 228 and two different phase comparators 224 and 226 having a common signal-input amplifier 222 and a common comparator input denoted as 221. The output of the VCO is connected directly to the comparator input 221. Phase comparator 224 is an exclusive-OR network and has a typical triangular phase-to-output response. With no signal or noise on the signal input, phase comparator 224 has an average output voltage equal to Vcc/2. Phase comparator 226 is an edge-controlled memory network which operates on the leading edges of the signal and comparator inputs. It continuously adjusts the VCO input voltage through the two-pole low-pass filter formed by capacitor $C_3$ and resistors $R_8$ and $R_9$ for equal frequency and phase of the signal and comparator inputs. With no signal input, the phase-locked loop 220 using comparator 226 adjusts the VCO 228 to its lowest possible frequency. The output of phase comparator 226 is a three-state output. Any time the phase comparator output is sinking or sourcing current into the low-pass filter the phase-pulses output is a logic 0. When the three-state output is in the high-impedance state the phase-pulses output is a logic 1.

In operation, the ECG signal from the output of the A/D converter 219 is fed into the signal-in input of the phase-locked loop 220, which is responsive to the QRS pulses of the ECG signal. The phase-locked loop locks onto regular QRS pulses, but is unable to lock in irregular QRS pulses. The output of the NOR-gate 230 goes low when the loop 220 is locked and goes high when the loop is unlocked. Inverter 232, capacitor $C_2$, diode $D_1$ and resistors $R_3$ and $R_4$ form an integrator 231. The integrator 231 integrates the output of NOR-gate 230. Capacitor $C_1$ provides a time delay, while resistors $R_3$ and $R_4$ adjust the rise and fall time, respectively, of the output of inverter 232. Inverters 234 and 236, and resistors $R_5$ through $R_7$ form a Schmitt trigger 233 having two switching thresholds; one near ground and the other near Vcc. The output of the Schmitt trigger appearing on line 235 is low when the loop 220 is locked and is high when the loop is unlocked.

The op-amp 238, capacitors $C_4$ and $C_5$, and resistors $R_{10}$ through $R_{12}$ form an active filter 229. Op-amp 240 and resistors $R_{15}$ and $R_{16}$ form a comparator 237. Op-amp 242 and resistors $R_{19}$ and $R_{20}$ form a comparator 239. The VCO input which is the voltage controlled oscillator's input is applied to the filter 229, which provides a D.C. voltage directly proportional to heart rate. The output of the filter 229 is fed to the pulse-input of comparator 237. The voltage divider formed by resistors $R_{13}$ and $R_{14}$ provides a reference voltage to the minus-input of comparator 237. The output of comparator 237 is low when heart rate is normal and goes high when heart rate is higher than normal. The output of filter 229 is also fed to the minus-input of comparator 239. The voltage divider formed by resistors $R_{17}$ and $R_{18}$ provides a reference voltage to the plus-input of comparator 239. The output of comparator 239 is low when heart rate is normal and goes high when heart rate is lower than normal.

The output of OR-gate 244 is low when all of the outputs from the Schmitt trigger 233 and the comparators 237 and 239 are low, and goes high when any of said outputs goes high. The high output of OR-gate 244 provides the signal on line 208 to enable the record/-playback device 184 and the signal on line 210 to cause the interval timer 212 to issue a time tag.

Obviously many modifications and variations of the present invention are possible in light of the above teachings. It is therefore to be understood that within the scope of the appended claims, the invention may be practiced otherwise than as specifically described.

What is claimed is:

1. Apparatus dedicated to a single patient for monitoring the operation of an automatic defibrillator implanted in the patient, the apparatus comprising:
    first detector means responsive to deliverance of defibrillating energy by said implanted defibrillator for triggering the storage of data related to said deliverance of the defibrillating energy;
    storage means for durably storing said data;
    external receiving means for receiving said data; and
    telemetry means for transmitting said data from the patient to said external receiving means.

2. The device recited in claim 1 wherein said storage means is implanted with said defibrillator.

3. The device recited in claim 1 wherein said storage means is external to the recipient.

4. The device recited in claim 1 wherein said are disturbances in cardiac electrical activity.

5. The device recited in claim 1 wherein said data are defibrillation pulses.

6. The device recited in claim 1 wherein said data is a representation of an ECG signal.

7. The device recited in claim 1 wherein said data is a time tag.

8. The device recited in claim 1 wherein said telemetry means is external to said recipient, and includes external electrodes on said recipient for sensing the electrical activity of the heart.

9. The device recited in claim 1 wherein said telemetry means is implanted with said defibrillator.

10. The device recited in claim 1 and further comprising means for permanently recording said data transmitted to said external receiving.

11. The device according to claim 1, wherein said storage means comprises:
    first storage means having a predetermined small capacity for temporarily storing and updating a small portion of said data; and
    second storage means for durably storing the portion of the data occurring after the deliverance of defibrillating energy.

12. The device according to claim 11 wherein said first storage means and said second storage means comprise the same storage device.

13. The device according to claim 11 wherein said receiving device includes a tape recorder having a tape for durably storing the data stored in said first storage means and said data stored in said second storage means.

14. The device according to claim 11 wherein said first storage means includes a random access memory.

15. The device according to claim 11 wherein said first storage means includes a shift register.

16. The device according to claim 11 wherein said first storage means and said second storage means each include a random access memory.

17. The device according to claim 1 further comprising means for converting said data into a digital signal, and means for delivering said digital signal to said receiving device.

18. The device of claim 1, further comprising second detector means responsive to events characteristic of a possible fibrillation episode for triggering the storage of data related to said possible fibrillation episode, and wherein said storage means durably stores said data related to said possible fibrillation episode, said external receiving means receives said data related to said possible fibrillation episode, and said telemetry means transmits said data related to said fibrillation episode from said patient to said external receiving means.

19. The device of claim 18, further comprising means for formatting said received data related to said possible fibrillation episode and said deliverance of defibrillating energy to provide information indicative of whether or not said deliverance of defibrillating energy was made in response to the detection of fibrillation by said implanted defibrillator.

20. The device of claim 1, further comprising means for monitoring data relating to cardiac electrical activity, and wherein said first detector means, in response to said deliverance of defibrillating energy, triggers the storage of data related to said cardiac electrical activity, said external receiving means receives said data related to said cardiac electrical activity, and said telemetry means transmits said data related to said cardiac electrical activity from said patient to said external receiving means.

21. The device of claim 20, further comprising means for formatting said received data related to said cardiac electrical activity and said deliverance of defibrillating energy to provide information indicative of whether or not said deliverance of defibrillating energy was made in response to the detection of fibrillation by said implanted defibrillator.

22. The device of claim 21, further comprising second detector means responsive to events characteristic of a possible fibrillation episode for triggering the storage of said data related to said cardiac electrical activity.

23. Apparatus dedicated to a single patient for recording data pertinent to the operation of an automatic defibrillator implanted in the patient, said apparatus comprising:
   means for sensing electrical activity associated with the patient's heart as a first signal;
   means for converting said first signal to a digital signal;
   first memory means having a predetermined number of memory locations for storing said digital signal;
   means responsive to said first signal for providing a fibrillation signal at the detection of fibrillation;
   detector means responsive to the deliverance of defibrillating energy into the patient's heart for producing a defibrillation signal;
   means responsive to said fibrillation signal for disabling said first memory means, and for causing said first memory means to hold the digital signal already stored therein;
   second memory means having a predetermined number of memory locations for storing said digital signal;
   means responsive to said fibrillation signal for enabling said second memory means; and
   means responsive to said defibrillation signal for enabling said second memory means.

24. The device according to claim 23 further comprising:
   first memory address means for addressing said memory locations in said first memory means;
   means responsive to said fibrillation signal for storing the address of said first memory means; and
   second memory address means for addressing said memory locations in said second memory means.

25. The device according to claim 23 further comprising means for reproducing in eye-readable format the portion of the first signal stored in said first and second memory means.

26. The device of claim 23 wherein said second storage means includes a tape recorder for durably storing the output of said first storage means.

27. Apparatus dedicated to a single patient for monitoring the operation of an automatic defibrillator implanted in the patient, the apparatus comprising:
   a first unit adapted to be worn by the patient, said first unit comprising,
   sensing means for sensing electrical activity associated with the patient's heart as a first signal, and
   transmitting means for transmitting said sensed first signal; and
   a second unit capable of easily being carried and moved, said second unit comprising,
   receiving means for receiving said transmitted first signal,
   detector means in circuit with said receiving means and responsive to a defibrillation attempt for triggering the storage of data related to said attempt, and
   storage means for durably storing said data related to said attempt.

28. The device of claim 27 wherein said detector means is an arrhythmia detector.

29. The device according to claim 27 wherein said second unit further comprises means for retrieving from said storage means said durably stored data related to said attempt, and
   means for displaying said retrieved output in eye-readable format.

30. The device according to claim 27 wherein said first unit further comprises internal timing means for providing a time tag, and means responsive to said detector means for causing said time tag to be durably stored in said storage means.

31. The device according to claim 30 wherein said internal timing means is a digital watch chip.

32. The device according to claim 27 wherein said sensing means is a set of chest electrodes.

33. The device according to claim 27 wherein said second unit further comprises:
   means responsive to said received first signal for producing a detection signal when said received first signal falls below a predetermined magnitude,
   audio means for producing an audible tone in response to said detection signal, and
   means operatively associated with said storage means for disabling said storage in response to said detection signal.

34. The device according to claim 27 further comprising means in circuit between said receiving means and said ECG storage means for converting said received ECG signal into a digital signal.

35. The device of claim 34 wherein said storage means includes a random access memory.

36. The device of claim 34 wherein said storage means includes a shift register.

37. The device of claim 27 wherein said first unit further comprises encoding means in circuit between said sensing means and said transmitting means for encoding said sensed first signal, and said second unit further comprises decoding means in circuit with said receiver means and said storage means for decoding said received first signal.

38. The device of claim 37 wherein said encoding means is a pulse frequency modulation encoder and said decoding means is a pulse frequency modulation decoder.

39. The device of claim 37 further comprising a pulse sensor means responsive to said sensed ECG signal for providing to said encoding means a defibrillation signal produced when said pulse sensor means senses a defibrillation pulse.

40. The device of claim 37 wherein said decoding means is also in circuit between said receiver means and said detecting means.

41. The device according to claim 27 wherein said storage means includes a cassette tape recorder having a magnetic tape.

42. The device according to claim 41 wherein said second unit further comprises means for retrieving the information stored on said magnetic tape, and means for displaying said retrieved information in eye-readable format.

43. The apparatus of claim 39, wherein said second unit further comprises,
   means responsive to said received first signal for producing a second signal when said received first signal falls below a predetermined magnitude, and
   means for producing an audible tone in response to said second signal to alert the patient that said first signal is not being received by said second unit.

44. Apparatus dedicated to a single patient for monitoring the operation of an automatic defibrillator implanted in the patient, the apparatus comprising:

first detector means responsive to events characteristic of a possible fibrillation episode for triggering the storage of data related to said possible fibrillation episode;

second detector means responsive to deliverance of defibrillating energy by said implanted defibrillator for triggering the storage of data related to said deliverance of defibrillating energy;

storage means for durably storing the data related to said possible fibrillation episode and said deliverance of defibrillating energy;

external receiving means for receiving the data related to said possible fibrillation episode and said deliverance of defibrillating energy; and telemetry means for transmitting the data related to said possible fibrillation episode and said deliverance of defibrillating energy from the patient to said external receiving means.

45. An implantable automatic defibrillator including treatment verification capabilities, said defibrillator comprising:

sensing means for sensing electrical activity associated with the heart of a wearer;

detector means receiving said electrical activity from said sensing means for detecting cardiac arrhythmias including fibrillation;

signal-generating means for issuing signals in response to the detection of arrhythmias by said detector means;

storage and discharge means for first storing and then automatically discharging defibrillating energy through the heart of the wearer;

charging means for charging said storage and discharge means with said defibrillating energy;

means creating an electrical link between said signal-generating means and said charging means for activating said charging means upon detection of fibrillation by said detector means;

storage means for durably storing the electrical activity sensed by said sensing means; and means creating an electrical link between said signal-generating means and said storage means for activating said storage means upon detection of an arrhythmia by said detector means.

46. The defibrillator of claim 45, wherein said storage and discharge means and said charging means are activated simultaneously in response to a single signal produced by said signal-generating means.

* * * * *